United States Patent
Thramann et al.

(10) Patent No.: US 7,175,623 B2
(45) Date of Patent: Feb. 13, 2007

(54) CERVICAL PLATE WITH BACKOUT PROTECTION

(75) Inventors: Jeffrey Thramann, Longmont, CO (US); Michael Fulton, Superior, CO (US); Spanky A. Raymond, Uniontown, OH (US)

(73) Assignee: Lanx, LLC, Boulder, CO (US)

( * ) Notice: Subject to any disclaimer, the term of this patent is extended or adjusted under 35 U.S.C. 154(b) by 198 days.

(21) Appl. No.: 10/932,272

(22) Filed: Sep. 1, 2004

(65) Prior Publication Data

US 2005/0027296 A1 Feb. 3, 2005

Related U.S. Application Data

(63) Continuation-in-part of application No. 10/632,760, filed on Aug. 1, 2003, which is a continuation-in-part of application No. 10/178,371, filed on Jun. 24, 2002, now Pat. No. 6,602,257.

(51) Int. Cl.
 *A61B 17/58* (2006.01)
(52) U.S. Cl. .............................. 606/69; 606/60; 606/61
(58) Field of Classification Search .................. 606/69, 606/60, 61
See application file for complete search history.

(56) References Cited

U.S. PATENT DOCUMENTS

| | | | |
|---|---|---|---|
| 4,794,918 A | 1/1989 | Wolter | |
| 5,085,660 A | 2/1992 | Lin | |
| 5,364,399 A | 11/1994 | Lowery et al. | |
| 5,558,674 A | 9/1996 | Heggeness et al. | |
| 5,578,034 A | 11/1996 | Estes | |
| 5,676,666 A | 10/1997 | Oxland et al. | |
| 5,741,258 A | 4/1998 | Klaue et al. | |
| 5,904,683 A | 5/1999 | Pohndorf et al. | |
| 5,951,558 A | 9/1999 | Fiz | |
| 5,954,722 A | 9/1999 | Bono | |
| 5,957,927 A | 9/1999 | Magee et al. | |
| 6,129,730 A | 10/2000 | Bono et al. | |
| 6,139,550 A | 10/2000 | Michelson | |
| 6,152,927 A | 11/2000 | Farris et al. | |
| 6,159,213 A | 12/2000 | Rogozinski | |
| 6,193,721 B1 | 2/2001 | Michelson | |
| 6,224,599 B1 | 5/2001 | Baynham et al. | |
| 6,224,602 B1 | 5/2001 | Hayes | |
| 6,235,033 B1 * | 5/2001 | Brace et al. ................... | 606/69 |
| 6,235,034 B1 | 5/2001 | Bray | |
| 6,258,089 B1 | 7/2001 | Campbell et al. | |
| 6,261,291 B1 | 7/2001 | Talaber et al. | |
| 6,306,139 B1 | 10/2001 | Fuentes | |
| 6,413,259 B1 | 7/2002 | Lyons et al. | |
| 6,436,101 B1 | 8/2002 | Hamada | |
| 6,503,250 B2 | 1/2003 | Paul | |
| 6,533,786 B1 | 3/2003 | Needham et al. | |
| 6,540,748 B2 | 4/2003 | Lombardo | |
| 6,626,907 B2 | 9/2003 | Blain et al. | |
| 6,695,846 B2 | 2/2004 | Richelsoph et al. | |

(Continued)

*Primary Examiner*—Cris L. Rodriguez
*Assistant Examiner*—Candice C. Stokes
(74) *Attorney, Agent, or Firm*—Holland & Hart LLP

(57) ABSTRACT

The present invention provides a cervical plate with backout protection. In particular, a bushing residing in each of a plurality of through holes has a bottom edge that aligns with a protrusion on a screw head. The bottom edge aligning with the protrusion inhibits reverse threading or backing out of the bone screw.

20 Claims, 5 Drawing Sheets

U.S. PATENT DOCUMENTS

| | | |
|---|---|---|
| 2002/0015189 A1 | 2/2002 | Miyajima |
| 2002/0120273 A1 | 8/2002 | Needham |
| 2003/0040749 A1 | 2/2003 | Grabowski |
| 2003/0060828 A1 | 3/2003 | Michelson |
| 2003/0078583 A1 | 4/2003 | Biedermann |

* cited by examiner

CERVICAL PLATE WITH BACKOUT PROTECTION

RELATED APPLICATIONS

This application is a continuation-in-part of U.S. patent application Ser. No. 10/632,760, filed Aug. 1, 2003, titled CERVICAL PLATE, which is a continuation in part of U.S. patent application Ser. No. 10/178,371, filed Jun. 24, 2002, titled CERVICAL PLATE, now U.S. Pat. No. 6,602,257.

FIELD OF THE INVENTION

The present invention relates to implantable devices useful in bone fusion and, more particularly, to cervical plates having backout protection.

BACKGROUND OF THE INVENTION

The vertebrae of the human spine are arranged in a column with one vertebra on top of the next. Between each vertebra exists an intervertebral disc that transmits force between adjacent vertebrae and provides a cushion between the adjacent vertebrae.

Sometimes, back pain is caused by degeneration or other deformity of the intervertebral disk ("diseased disk"). Conventionally, surgeons treat diseased discs by surgically removing the diseased disc and inserting an implant in the space vacated by the diseased disk, which implant may be bone or other biocompatible implants. The adjacent vertebrae are then immobilized relative to one another. Eventually, the vertebrae grow into one solid piece of bone.

Currently, it is difficult to insert the bone graft into the vacated space and fuse the adjacent vertebrae. The current process of inserting a bone graft and fusing the adjacent vertebrae will be explained with referring to FIGS. 1 and 2. FIG. 1 shows two adjacent vertebrae 102 and 104. Located between vertebrae 102 and 104 is an intervertebral space 106 partially filled by an implant 108. When the implant 108 is first inserted into the intervertebral space 106, the adjacent vertebrae 102 and 104 are manually kept apart by the surgeon using, for example, a retracting device (not shown). As shown in FIG. 2, once the implant 108 is placed, the surgeon releases the adjacent vertebrae 102 and 104 allowing them to squeeze the implant 108 and hold the implant 108 in place.

To immobilize the vertebrae 102 and 104 with the implant 108 in place, the surgeon next applies a cervical plate 202 over the adjacent vertebrae 102 and 104. Cervical plate 202 may have a central viewing window 204 and one or more screw holes 206, in this example four screw holes 206a–206d are shown. Four bone screws (which will be identified by reference numerals 208a–208d) would be screwed into the vertebrae using the screw holes 206 to anchor the cervical plate to the vertebrae and immobilize the vertebrae with respect to one another.

The bone screws 208a–208d absent a locking mechanism tend to reverse thread, which is also known as backing out. Locking mechanisms have been developed to inhibit the bone screws from backing out. Some of the devices included caps or plates that extend over the screw holes 206 to inhibit upwards movement of bone screws 208a–208d. Other devices include a frictional engagement between a bushing and the bone screws 208a–208d.

Although many devices exist that satisfactorily inhibit backout of the bone screws, it would be desirous to develop a device to inhibit the bone screws from backing out.

SUMMARY OF THE INVENTION

To attain the advantages and in accordance with the purpose of the invention, as embodied and broadly described herein, a cervical plate having backout protection is provided. The cervical plate comprises a plurality at through holes. Each through hole includes a channel in which a bushing resides. The bushing has a bottom edge that can align with a protrusion on a screw head that inhibits the screw from backing out.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
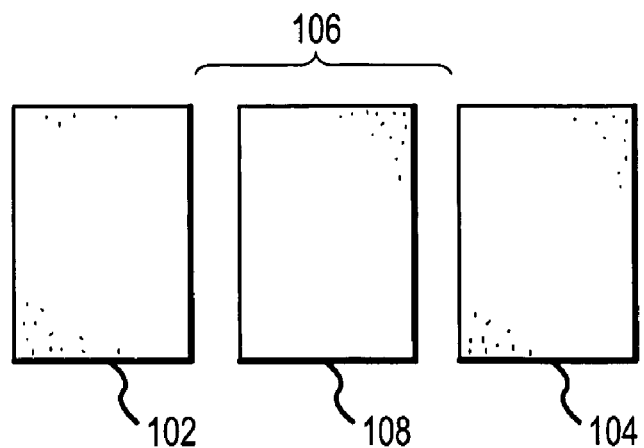
FIG. 1 shows adjacent vertebrae with a bone graft.
Figure 2:
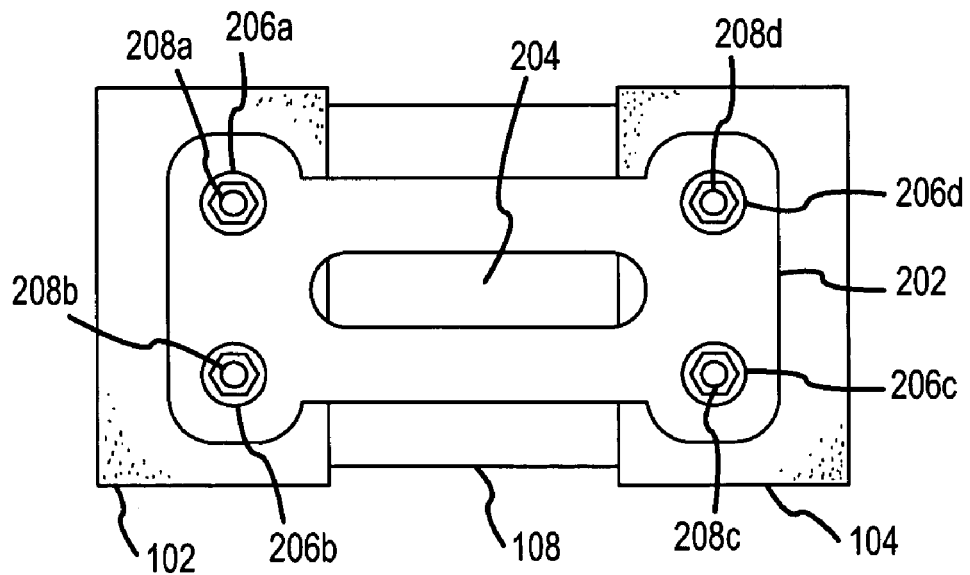
FIG. 2 shows adjacent vertebrae with a bone graft and cervical plate.
Figure 3:
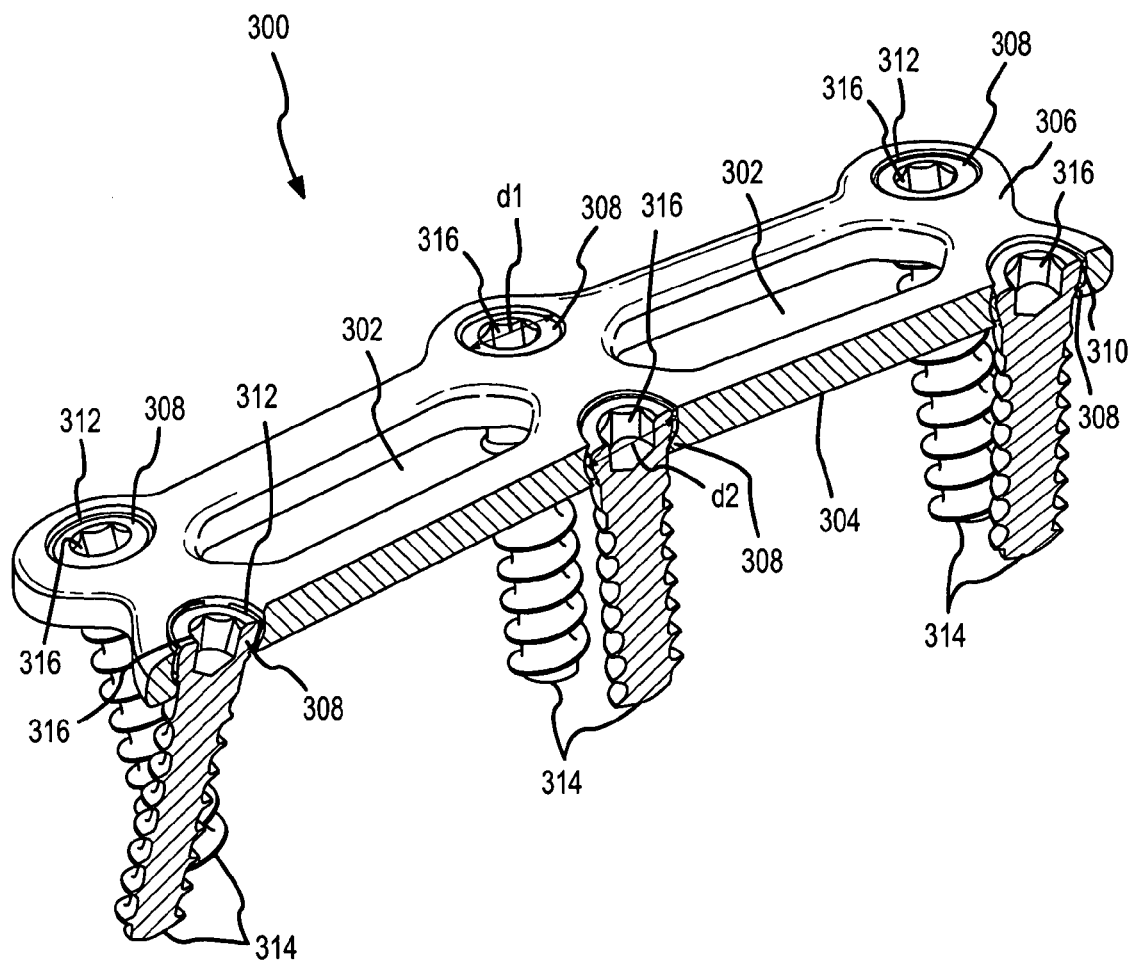
FIG. 3 shows a perspective and cross-sectional view of a cervical plate with backout protection consistent with the present invention.

The present invention will be described with reference to FIGS. 3–8. Referring first to FIG. 3, a perspective and cross-sectional view of a cervical plate 300 illustrative of an embodiment of the present invention is shown. Cervical plate 300 is shown with a construct that could span two intervertebral spaces (a.k.a. a two level cervical plate); however, cervical plate 300 could be constructed to span more or less intervertebral spaces. Because plate 300 spans two intervertebral spaces, cervical plate 300 is shown with two viewing windows 302. More or less viewing windows 302 could be provided. For example, for a construct that spanned one intervertebral space, only one viewing window may be used. Moreover, for a construct that spanned three intervertebral spaces, three viewing windows may be provided. Furthermore, for cervical plate 300, each viewing window 302 could be split into several smaller viewing windows as a matter of design choice.

Cervical plate 300 comprises a bone facing side 304, a top side 306 opposite bone facing side 304, and a plurality of through holes 308. Through holes 308 generally have a diameter d1, at least at bone facing side 304 and top side 306. Each of the plurality of through holes 308 has a channel 310 traversing a perimeter of through hole 308. Channel 310 resides between bone facing surface 304 and top side 306.

Generally, channel 310 has a concave shape with a maximum diameter of diameter d2 greater than d1. While described separately, channel 310 may simply be a bowing or gradual increase in diameter along the sidewalls associated with through holes 308. A bushing 312 resides in channel 310, as will be explained further below. Bone screws 314 extend through through holes 308 such that bone screws 314 are threaded to vertebral bodies. A head 316 of bone screws 314 engage bushings 312, as will be explained further below, inhibiting bone screws 314 from reverse threading or backing out.

Figures 4, 5:
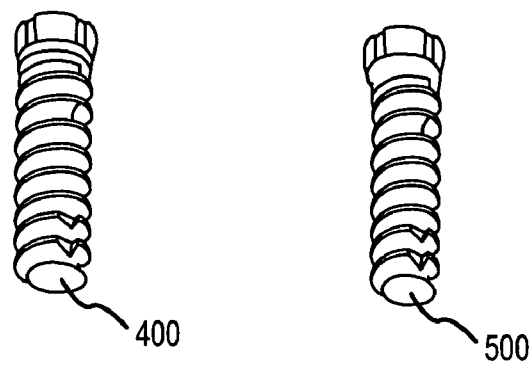
FIG. 4 shows a perspective view of a fixed angle bone screw.
FIG. 5 shows a perspective view of a variable angle bone screw.

Referring to FIGS. 4 and 5, fixed angle bone screw 400 and variable angle bone screw 500 are shown. Note, bone screws 314 could be either fixed angle bone screws 400 or variable angle bone screws 500, and both are shown in FIG. 3. Fixed angle bone screws 400 and variable angle bone screws 500 are generally known in the art and will not be further explained herein. Head 316 will be explained further below with reference to FIG. 7.

Figure 6:
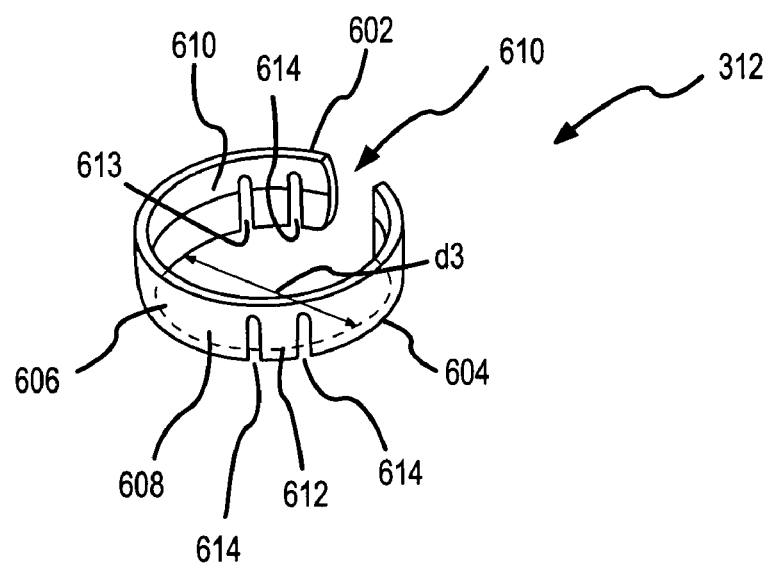
FIG. 6 shows a perspective view of an embodiment of one possible bushing consistent with the present invention.

Referring to FIG. 6, a perspective view of bushing 312 is shown in more detail. Bushing 312 comprises a top edge 602, which would be located proximate top side 304, and a bottom edge 604, which would be located proximate bone facing surface 306. Sidewall 606 extends between top edge 602 and bottom edge 604. Bushing 312 is shown generally cylindrical in shape but generally would have a shape consistent with channel 310 to allow cervical plate 300 and bone screws 314 to align properly during surgery. In this case, channel 310 has a concave shape to cooperatively engage a convex shape of an outer surface 608 of sidewall 606. Inner surface 610 has a shape consistent with heads 316. Outer surface 608 has a diameter d2 at its maximum. Bushing 312 is compressible such that bushing 312 can be compressed to fit within diameter d1. To assist with compression, bushing 312 may have a gap 610. Once the compressive force is removed, bushing 312 would expand such that outer surface 608 cooperatively engages channel 310.

At least a bottom portion 612 of bushing 312 comprises a flexible material that can expand outward when impinged by head 316, which will be explained further below. To facilitate the flexible movement, bottom portion 612 may comprises one or more slots 614. When not impinged by head 316, bottom edge 604 has a diameter d3.

Head 316 will be explained in more detail with reference to FIGS. 7 and 8. Head 316 has an internal matting surface 702. Internal matting surface 702 is designed to allow a surgical tool to drive bone screw 314 into a vertebral body. Head 316 has an external surface 704 that cooperatively engages inner surface 610 of bushing 312. In this case, inner surface 610 is concave and external surface 704 is convex. External surface 704 may extend over a portion or all of head 316, but terminates at a transition edge 706 where a protrusion 708, which may be a ledge or shoulder, extends. Transition edge 706 has a diameter d3 and protrusion 708 extends outward from transition edge 706 such that bottom edge 604 abuts protrusion 708. Thus, bushing 312 inhibits reverse threading of bone screw 314 because bottom edge 604 abutting protrusion 708 inhibits upward movement of bone screw 314. While bottom edge 604 could directly abut protrusion 708, washers or other devices could be implanted as well.

Figure 7:
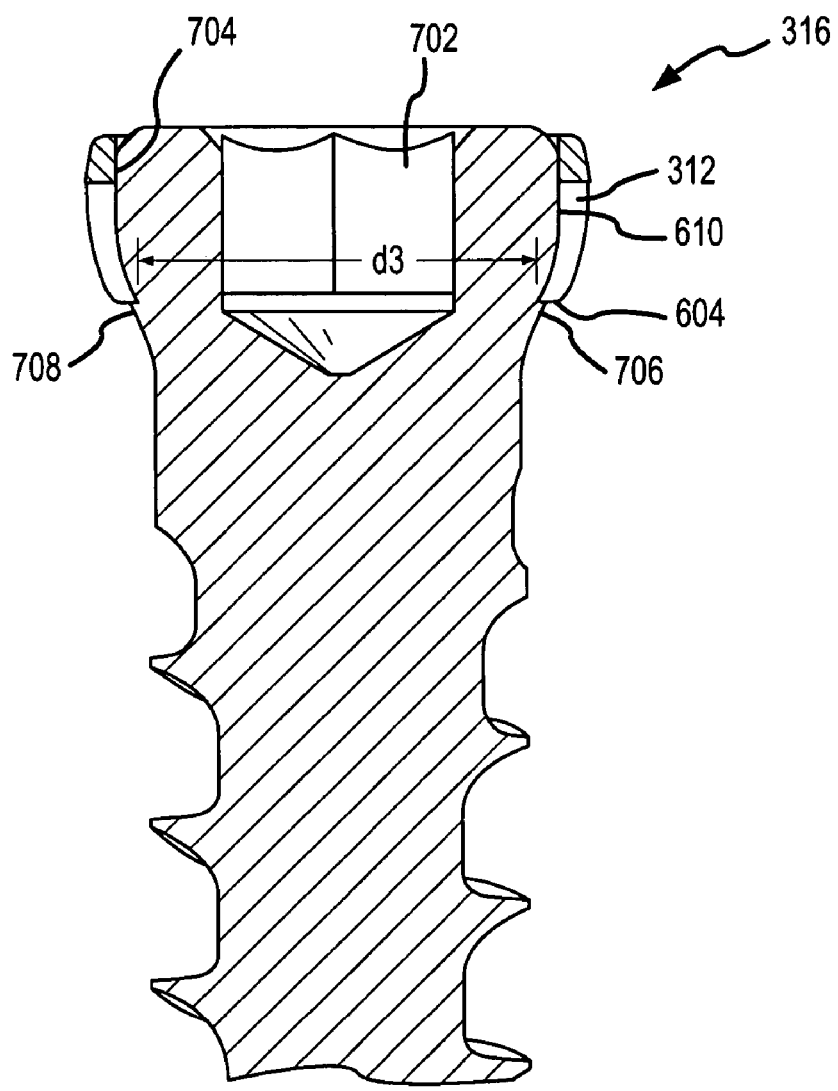
FIG. 7 shows a cross-sectional view of the bone screw and bushing as it would exist if the bone screw was threaded in the vertebral body.
Figure 8:
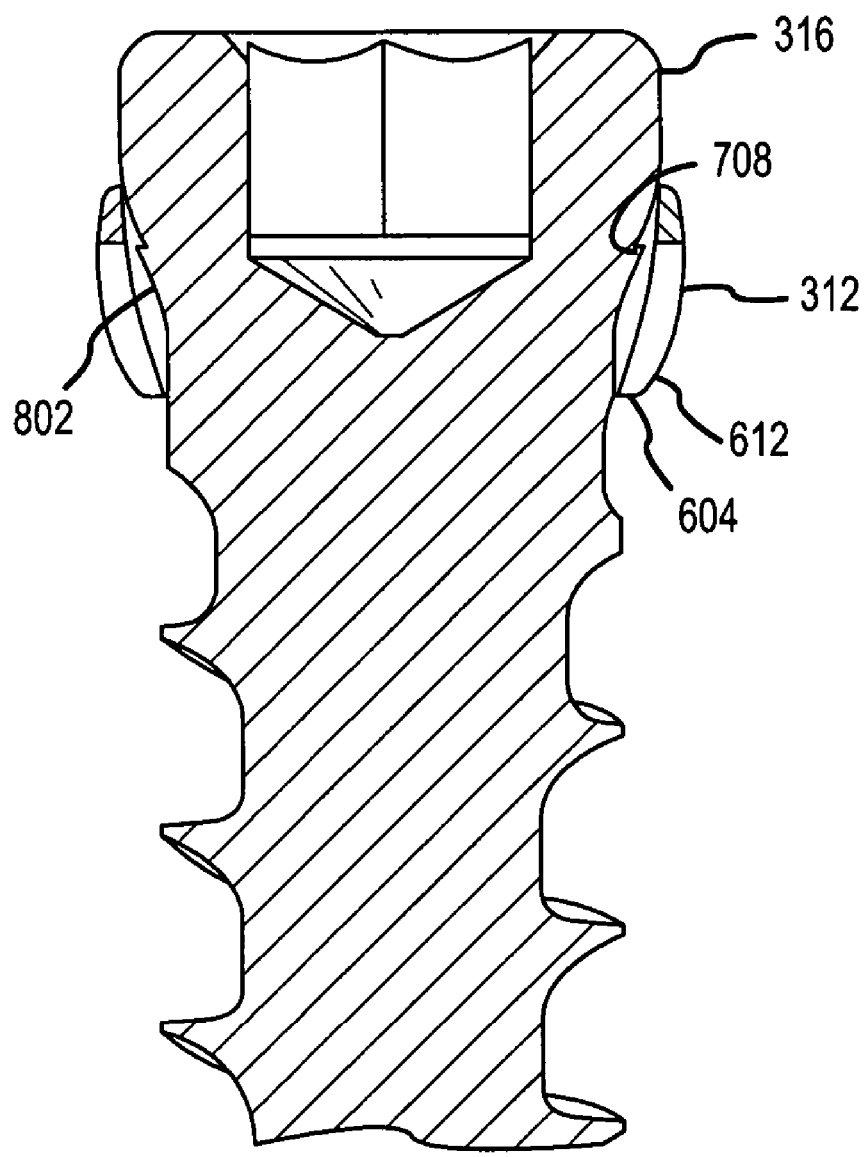
FIG. 8 shows a cross-section view similar to FIG. 7 but prior to complete engagement.

While FIG. 7 shows the implant after bone screw 314 has been threaded in the vertebral bodies, FIG. 8 shows the implant prior to completion of the threading operation. As bone screw 314 is threaded in the vertebral bodies, head 316 advances through bushing 312. A surface 802 on protrusion 708 tends to impinge on bottom portion 612 as head 316 advances. The impingement causes bottom portion 612 to flex. Once protrusion 708 advances past bottom edge 604, bottom portion returns to it pre-flex position such that bottom edge 604 is aligned over protrusion 708.

While the invention has been particularly shown and described with reference to an embodiment thereof, it will be understood by those skilled in the art that various other changes in the form and details may be made without departing from the spirit and scope of the invention.

We claim:

1. A device useful in bone fusion, comprising:
a cervical plate;
a plurality of through holes provided in the cervical plate;
each of the plurality of through holes comprising a channel;
a bushing residing in the channel;
the bushing comprising a shape that cooperatively engages the channel and a flexible bottom portion terminating in a bottom edge, whereby a head of a bone screw forces the flexible bottom portion outward as the bone screw is threaded, the bushing returning to an un-flexed position when the head is threaded through the bushing such that the bushing is not fixedly engaged with the channel and a protrusion on the head substantially aligns with the bottom edge, the protrusion and the bottom edge cooperatively engage to inhibit the bone screw from reverse threading.

2. The device of claim 1, wherein the channel is formed by an increase in diameter of the through hole.

3. The device of claim 2, wherein the increase in diameter forms a concave shape.

4. The device of claim 3, wherein the shape of the bushing is convex to cooperatively engage the channel.

5. The device of claim 1, wherein the bushing further comprises a gap, the gap allowing the bushing to be compressed between a first size where the bushing cooperatively engages the channel and a second size where the bushing is sufficiently compressed to fit in the through hole.

6. The device of claim 1, wherein the flexible bottom portion comprises at least one slot to facilitate the outward movement when the head impinges the bushing.

7. The device of claim 1, wherein the bushing cooperatively engages the channel allowing orientation of the bone screw.

8. A device useful in bone fusion, comprising:
a cervical plate;
a plurality of through holes provided in the cervical plate;
a plurality of bone screws provided to be inserted through the plurality of through holes, each of the plurality of bone screws comprising a head with a protrusion;
each of the plurality of through holes comprising a channel the channel comprising a channel shape;
a bushing residing in the channel;
the bushing comprising an outer shape that cooperatively engages the channel, an inner shape, and a flexible bottom portion terminating in a bottom edge; and
the head of each of the plurality of bone screws shaped to cooperatively engage the bottom edge of the bushing;
whereby during threading of the at least one bone screw, the protrusion impinges on the flexible bottom portion such that the protrusion passes the bottom edge wherein the flexible bottom portion returns to an un-flexed position and the bottom edge substantially aligns with the protrusion to inhibit the bone screw from reverse threading without fixedly engaging the plurality of through holes provided in the cervical plate.

9. The device of claim 8, wherein the at least one bone screw is a fixed angle bone screw.

10. The device of claim 8, wherein the at least one bone screw is a variable angle bone screw.

11. The device of claim 8, wherein the channel is formed by an increase in diameter of the through hole.

12. The device of claim 11, wherein the channel shape is concave and the outer shape is convex.

13. The device of claim 8, wherein the inner shape is concave and the head shape is convex.

14. The device of claim 12, wherein the inner shape is concave and the head shape is convex.

15. The device of claim 8, wherein the flexible bottom portion comprises at least one slot to facilitate the outward flexing of the flexible bottom portion when the head impinges on the flexible bottom portion.

16. The device of claim 8, wherein the bushing has an uncompressed state and a compressed state, wherein when in the uncompressed state the bushing cooperatively engages the channel and in the compressed state the bushing fits in the through hole.

17. The device of claim 16, wherein the bushing comprises a gap to facilitate compression of the bushing.

18. The device of claim 8, wherein the bone screw further comprises a surface that facilitates the flexing of the flexible bottom portion.

19. A method for placing an implant useful in fusing bone, the method comprising the steps of:
   compressing a bushing;
   inserting the compressed bushing through a channel in a fusion plate
   aligning the bushing with a channel;
   releasing the bushing such that the compressed bushing uncompresses and cooperatively engages the channel;
   inserting a bone screw through the through hole;
   threading the bone screw through the through hole;
   impinging a protrusion on the bushing causing the bushing to flex and allow the protrusion to advance through the bushing;
   passing the protrusion past the bushing causing the bushing to return to the un-flexed position: and
   aligning the protrusion below a bottom edge of the bushing such that the reverse threading of the bone screw is inhibited by the protrusion aligned with the bottom edge of the un-flexed bushing, and the un-flexed bushing not fixedly engaged with the through hole.

20. The method of claim 19, further comprising the step of orienting the bushing in the channel prior to inserting the bone screw to facilitate threading the bone screw.

* * * * *